United States Patent [19]

Craubner

[11] Patent Number: 4,813,283

[45] Date of Patent: Mar. 21, 1989

[54] DENSITY MEASURING APPARATUS

[75] Inventor: Hans Craubner, Stuttgart, Fed. Rep. of Germany

[73] Assignee: Max-Planck-Gesellschaft zur Foerderung der Wissenschaften e.v., Fed. Rep. of Germany

[21] Appl. No.: 188,127

[22] Filed: Apr. 22, 1988

Related U.S. Application Data

[63] Continuation of Ser. No. 897,409, Aug. 18, 1986, abandoned.

[30] Foreign Application Priority Data

Aug. 16, 1985 [DE] Fed. Rep. of Germany ....... 3529490

[51] Int. Cl.$^4$ ............................................. G01N 9/08
[52] U.S. Cl. ........................................ 73/436; 73/437
[58] Field of Search ................. 73/433, 434, 435, 436, 73/437

[56] References Cited

U.S. PATENT DOCUMENTS

3,246,524  4/1966  Shiba .
4,320,658  3/1982  Hilton et al. .

FOREIGN PATENT DOCUMENTS

919449  2/1963  United Kingdom ................. 73/433
1195734  6/1970  United Kingdom ................. 73/437

OTHER PUBLICATIONS

F. Kohlrausch, *Praktische Physik*, vol. 1, (B. G. Taubner, Stuttgart, 1985), pp. 362-374.
O. Kratky et al., "Dichtmessungen an Fluessigkeiten und Gasen etc.", *Z. Angew, Physik*, vol. 27 (1969), pp. 273-277.
N. Bauer et al., "Determination of Density", In: Weissberger et al., *Physical methods of Chemistry*, vol. I, (Wiley-Interscience, New York, 1972), pp. 57-124.
O. Kratky et al., "The Determination of the Partial Specific Volume of Proteins by the Mechanical Oscillator Technique", *Methods of Enzymology*, vol. 27 (1973), pp. 98-110.
J. Fortier et al: "Direct Continuous Measurements of Thermal Expansion coefficients etc.", *Review of Scientific Instruments*, 50 (11), Nov. 1979, pp. 1474–1480.

*Primary Examiner*—John Chapman
*Attorney, Agent, or Firm*—Handal & Morofsky

[57] ABSTRACT

A density measuring apparatus (densitometer) useful for rapid absolute determination of the density, the temperature dependence of density, partial volume and thermal expansivity of condensed matter, based on the hydrostatic method, employs an electronic balance enclosed in an airtight envelope which forms a weighing chamber and a measuring chamber. The balance comprises a balance beam and measuring and weighing hangdown assemblies attached to opposite ends of the beam. The balance beam and the weighing hangdown assembly are positioned in the weighing chamber. The measuring hangdown assembly extends from the weighing chamber into the measuring chamber and comprises a thin suspension wire and a sample support or a sinker which are positioned in a multi-jacket measuring vessel adapted to receive a buoyant or sample liquid. A vapor barrier is provided between the weighing and measuring chambers to prevent vapors of the buoyant or sample liquid from flowing into the weighing chamber.

20 Claims, 6 Drawing Sheets

DENSITY MEASURING APPARATUS

This application is a continuation of application Ser. No. 897,409 filed Aug. 18, 1986, now abandoned.

The present invention relates to devices for measuring parameters of condensed matter (liquids, solids) which are related to the density (ratio of mass to volume), more specifically to a density measuring apparatus ("densitometer") useful for rapid absolute determination of the density, the temperature dependence of density, partial volume and thermal expansivity of condensed matter based on the hydrostatic method.

BACKGROUND OF THE INVENTION

The density of a substance, i.e. the mass per unit volume (as grams per cubic centimeter) is one of the most important intensive parameters of a material. The density of condensed matter, such as solids and liquids, and the pressure and/or temperature dependency of the density is of paramount importance for many scientific and technical investigations.

A well known method for the determination of density is the so-called hydrostatic density measurement method. This method is an application of the familiar Archimedes' hydrostatic buoyancy principle and involves the measurement of the upward buoyant force exerted on a body immersed in a fluid of less density as that of the immersed body. The hydrostatic method furnishes the most precise and reliable density values, especially in case of solids, and may be performed with an electronic balance comprising a balance beam coupled to a force measuring system, and a pair of hangdown assemblies supported by the opposite ends of the balance beam. The hangdown assemblies may comprise thin suspension wires and sample and compensating weight supports for supporting a solid sample and a compensating weight, respectively. The sample support generally comprises a pair of sample pans suspended one above the other within a measuring chamber which can be filled with the buoyant liquid up to such a level that the lower pan is immersed in the liquid while the upper pan is above the surface of the liquid. A sinker body is substituted for the immersed weighing pan when the density of a liquid sample is to be measured which in this case is used as buoyant liquid.

It is generally quite difficult, to obtain accuracies in the order of the fourth or fifth or higher decimal place with the known densitometers. This applies specifically if the mass of the sample is small, as below 1 gram, and if the density measurements have to be performed at temperatures differing essentially from the normal room temperature (21° C.) or within an extended temperature range. Further, the known densitometers do not allow fast measurements, as it is specifically desired when a functional dependency of the density on the temperature, the concentration, the molecular structure or variation of the structure are to be measured with sufficient accuracy and within a reasonably small period of time.

BRIEF DESCRIPTION OF THE INVENTION

The present invention provides a densitometer apparatus which avoids the above discussed drawbacks of the prior art and allows to perform measurements of the absolute value of the density with higher accuracy and within a shorter period of time at temperatures differing essentially from the normal room temperature and/or temperatures within an extended temperature range.

A densitometer apparatus according to a preferred embodiment of the invention comprises an airtight envelope connectable to a gas and vacuum system and enclosing an electronic balance. The electronic balance comprises a balance beam coupled to an electronic force measuring device. First and second (measuring and weighing) hangdown assemblies are mounted on the opposite ends of the balance beam. The first or measuring hangdown assembly comprises a sample support (or alternatively a sinker body) suspended from the beam by a thin wire. The sample support may comprise a pair of stirrup pans for receiving a solid sample. The second hangdown assembly comprises a single stirrup pan for receiving a compensation weight.

The measuring hangdown assembly extends into a measuring or sample chamber which comprises a multijacket vessel portion of the measuring chamber and is adapted to receive a buoyant or a sample liquid. According to the invention, a semipermeable, quasi-adiabatic barrier or "wall" is provided between the measuring chamber portion of the envelope and the remaining weighing chamber portion of the envelope which latter contains the balance beam and the weighing hangdown assembly. The semipermeable, quasi-adiabatic barrier allows an exchange of permanent gases between the measuring chamber and the weighing chamber but prevents the flow of vapors of the buoyant or sample liquid from the measuring chamber into the weighing chamber.

The present new densitometer device allows very accurate and quick measurements of the absolute value of the density, the temperature dependency of density, partial volumes and expansivity in a large temperature range, e.g. down to at least about $-100°$ C., and up to at least about 300° C. Also sensitive substances can be measured, regardless of form and shape, i.e. powders, granulated materials, fibers, films and many other types of solid materials and liquids including solutions.

For a direct determination of the absolute value of the density, a calibration standard of fused silica having a simple configuration, as that of a cylinder, may be used. By use of scanning techniques, density measurements can be carried out in a direct, continuous mode amenable to automation.

The barrier means allows an exchange of permanent gases between the measuring chamber and the weighing chamber, that is between a protective gas such as nitrogen or a noble gas, such as helium or argon. It prevents, however, that condensable gases and/or vapors, from the buoyant or sample liquid contained in the measuring chamber, can flow from the measuring chamber into the weighing chamber. Thus, a flow of condensable matter and heat energy from the measuring chamber into the weighing chamber and a flow of heat energy from the weighing chamber into the measuring chamber are essentially prevented when the system has attained its thermal equilibrium. Allowed, in some cases even desired is, however, a flow of material in form of protective gas in the direction from the weighing chamber to the measuring chamber in case of a variation of the thermodynamic state in the measuring and/or weighing chambers. The barrier means allows to vary the temperature in the measuring chamber within wide limits while the measuring pressure is maintained constant, independent of the specific thermodynamic conditions within the weighing chamber which preferably are held constant during the entire measuring cycle, preferably on constant pressure and normal room temperature.

Various buoyant liquids can be used, e.g. n-hexane, isopentene, toluene, carbon tetrachloride, 1,1,2,2-tetrabromo ethane, liquified gases as liquid argon or nitrogen, further, liquids having a high boiling point, such as oils, e.g. silicone oil.

Accurate measurements can be performed also with small sample masses, e.g. from 1 to 1000 mg, the preferred range being about 5 to 500 mg in the case of solids and 6 to 100 $cm^3$ in the case of liquids.

An important advantage of the densitometer according to the invention is that the measurements can be performed also in a dynamic mode, i.e. continuously or quasi-continuously or with a step-wise temperature variation similar to a scanning method, and with a temperature gradient as controlling thermodynamic parameter. This is of specific advantage when phase transitions, variations of the molecular structure and the like are to be investigated, e.g. when the properties of arorphous or partially amorphous-crystaline solids, as metallic "glasses", ceramic materials, polymer materials, liquid or solid multi-component systems, phase separations in such systems, solution and hydration effects and so on are to be investigated.

DESCRIPTION OF A PREFERRED EMBODIMENT

Figure 1:
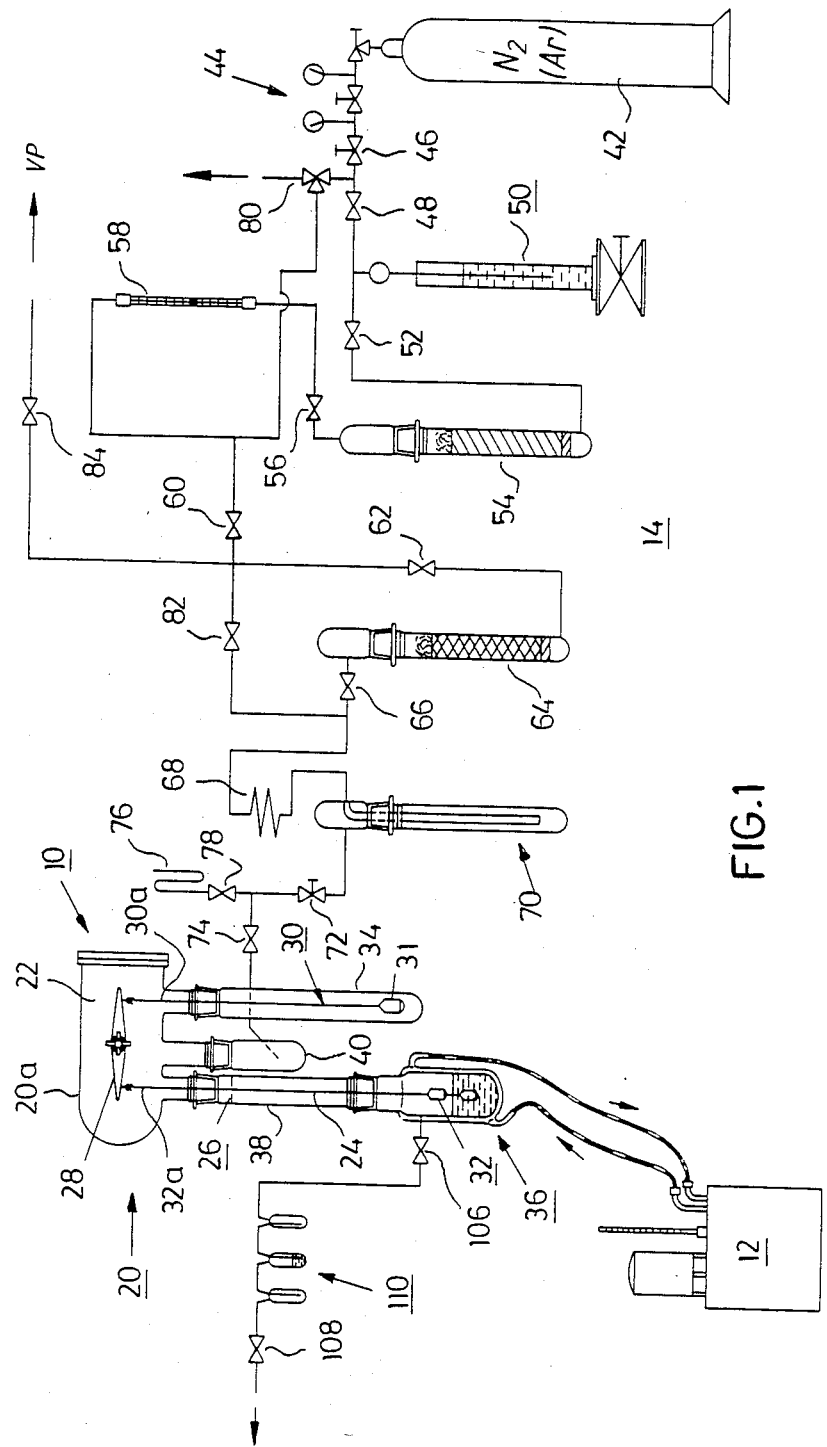
FIG. 1 is a diagrammatic view of essential portions of a density measuring apparatus comprising an embodiment of the present invention.

FIG. 1 shows a portion of a density measuring system which includes essentially three sections:

1. An electronic measuring and force-sensing system of an electronic balance 10, 2. A system 12 for controlling, regulating and measuring temperatures employed during the measurements, and 3. A protective gas and vacuum system 14.

Further, the apparatus comprises an electronic system for controlling, data acquisition, data processing, display and recording which will be explained in some detail below with reference to FIG. 2.

Figure 5:
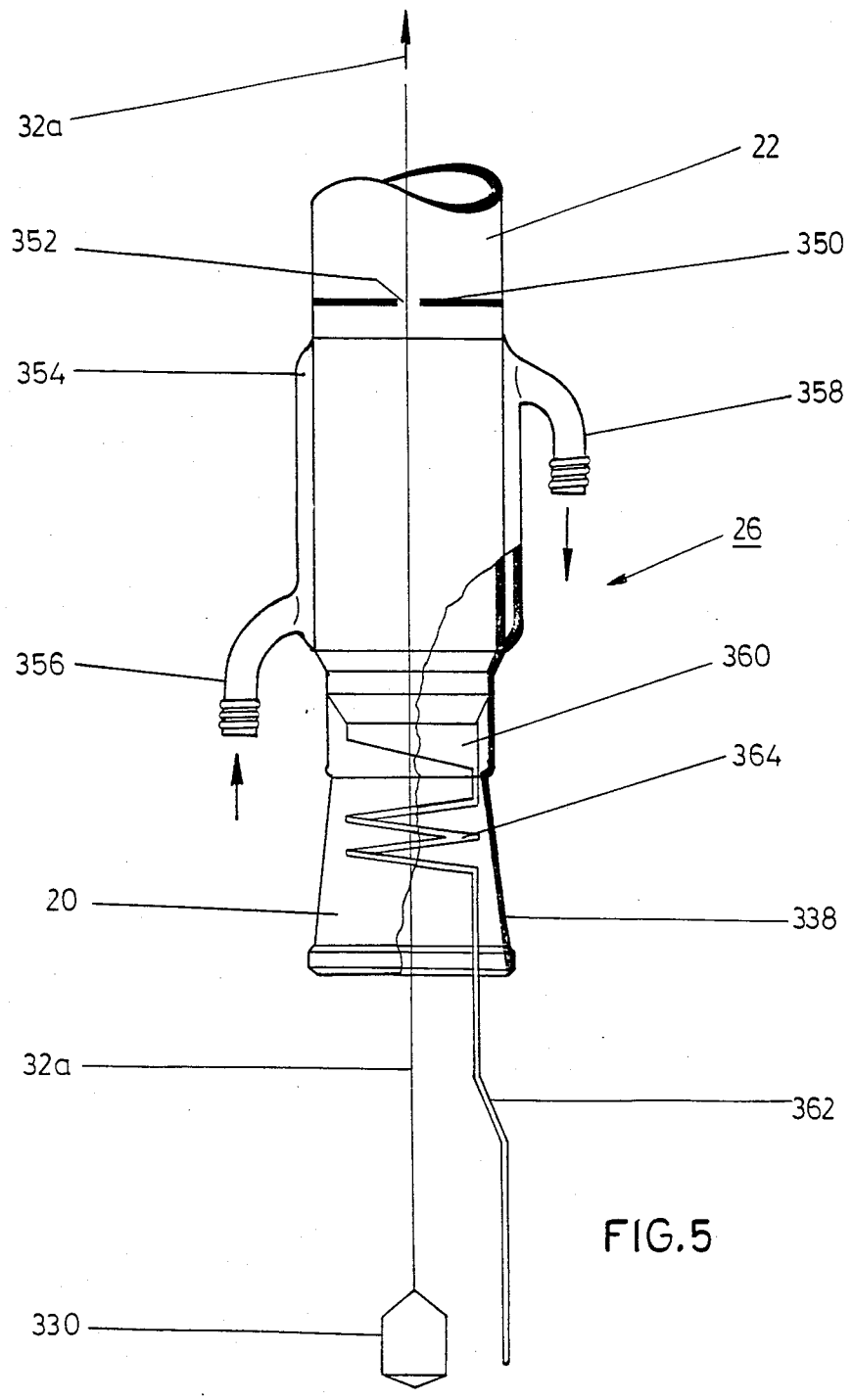
FIG. 5 is a detailed view of a thermodynamic separator or barrier means of the apparatus of FIG. 1.

The electronic balance 10 may comprise a known device, e.g. a device operating on the principle of electro- magnetic force compensation (Cahn RG, Cahn Instruments Inc., Cerritos Calif.) which is modified as will be explained below. The measuring portion of the electronic balance comprises an airtight envelope 20 forming a weighing chamber 22 and a measuring chamber 24. According to an essential feature of the present invention, a separator or barrier device 26 which will be explained in detail with reference to FIG. 5 is provided between the measuring and weighing chambers.

A balance beam 28 is mounted within a main portion 20a of the envelope 20. The portion 20a forms part of the weighing chamber 22. The beam is rotatably supported at its center, forms a portion of a force sensing system of the balance and has two arms extending in opposite directions. A weighing hangdown assembly 30 and a measuring hangdown assembly 32 are suspended from the opposite ends of the balance beam 28. The hangdown assemblies comprise delicate wires 30a, 32a, respectively, or similar suspension means. The wires may have a diameter of about 0.1 mm and may be made e.g. of Cr-Ni or Au-Ni or Pt-Ir alloy.

The weighing hangdown assembly 30 further comprises a weighing pan 31 for supporting compensation or reference weights and is enclosed by a protective tube portion 34 of the envelope 20. The bottom end of the protective tube portion 34 is closed, the upper end is connected by a ground joint to the main portion 22 of the envelope. The measuring hangdown assembly 32 extends downwards into a multi-jacket measuring vessel 36 which forms a portion of the measuring chamber 24 and will be explained in more detail with reference to FIG. 3. The upper end of the measuring vessel 36 is connected by a ground joint to the lower end of a protective tube 38 through which the wire 32a of the measuring hangdown assembly extends. The upper end of the tube 38 is connected to the main portion 20a by another ground joint. The main portion 20a is further provided with connection tube 40 means which is coupled with the vacuum and protective gas system 14. The system 14 serves primarily to provide within the envelope 20 a desired atmosphere, e.g. protective gas atmosphere having a water vapor content as low as possible and a predetermined, constant pressure. The parts 20a, 34, 36, 38 and 40 of the envelope are preferably made of borosilicate glass and coupled by ground joints in a vacuum-tight and disconnectable manner.

The vacuum and protective gas system 14 comprises a container 42, as a pressurized gas cylinder containing a protective gas, such as nitrogen or a noble gas, e.g. argon or helium. The container 42 is coupled through pressure reducing valve means 44 and shutoff valve means 46, 48 to an immersion tube system 50 containing e.g. glycerol or mercury and serving for pressure control. Then follow, in flow direction towards the envelope 22, a shutoff valve 52, a first drying column 54 which may comprise silicagel, a shutoff valve 56, a flow meter 58, shutoff valves 60, 62, a second drying column 64 which may comprise a molecular sieve (4 Å, Merck, Darmstadt/Germany), a shutoff valve 66, a glass tube spring element 68, a cooling trap 70 which may comprise liquid nitrogen, a control valve 72 and a shutoff valve 74. A pressure measuring device 76 is coupled to the connection of the valves 72 and 74 via a shutoff valve 78.

A first port of a three-way valve 80 is coupled to the connection of the valves 46 and 48. A second port of the valve 80 opens into the atmosphere and a third port is connected to the connection of the flowmeter 58 and the valve 60 so that the units 50, 54 and 58 can be bypassed. The connection of the valves 60 and 62 is coupled by a bypass valve 82 which allows to bypass the column 64, to the connection between the valve 66 and the spring element 68, and is further coupled through a shutoff valve 84 to a vacuum pump VP, not shown.

The measuring chamber 24 comprising the vessel 36 is coupled to the atmosphere through the series connection of a shutoff valve 106, an immersion tube system 110, and a further shutoff valve 108.

The vacuum and protective gas system described above allows measurement in a vacuum environment and in various gas atmospheres. The pressure of the gas atmospheres may vary between a partial vacuum and some pressure above atmosphere pressure, e.g. from 2 to 10 kPa excess pressure.

Figure 2:
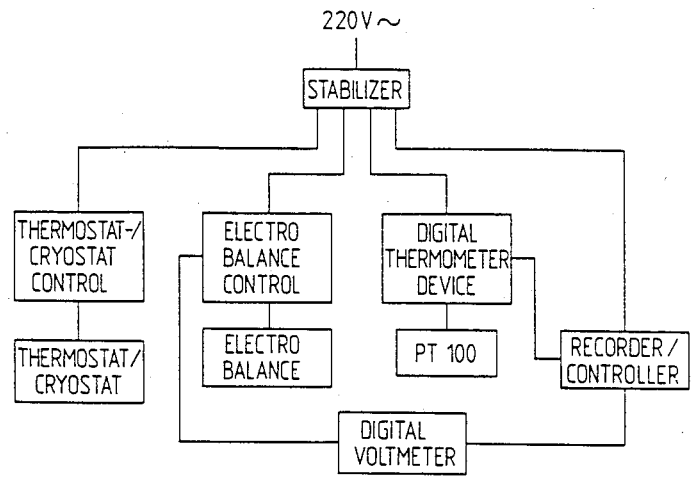
FIG. 2 is a block diagam of an electronic control and display system for the apparatus of FIG. 1.

The electronic system shown in FIG. 2 comprises a regulated power supply (stabilizer) 90 (type WS-10 Wandel & Goltermann, Reutlingen/Germany) energized by the a.c. mains and providing regulated operating voltages to the various units of the apparatus. A thermostat and cryostat control unit 92 controls a thermostat/cryostat system which form part of the unit 12 (FIG. 1). The system 12 may comprise a pair of ultrathermostats connected in series (Dr. Wobser KG, Lauda-Königshofen/Germany, types NBS-D for temperatures of +10° to +100° C., HBS-HT for temperatures between about +50° to about 300° C.; accuracy around room temperature better than 0.05K). Low temperatures experiments may be carried out by use of ultracryostats (Colora Mebtechnik, Lorch/Wuerttemberg/Germany, type KT 80 S, temperature range about −80° to +20° C.). A platinum resistance thermometer 96 (PT100, German standard DIN 43760) is provided for temperature measurements. The thermometer 96 is coupled to a digital temperature measuring device (Dr. Wobser KG, type R46 with 10-channel selector switch, indication accuracy at 0° C. about 0.01K). The electronic balance 10 is coupled to an electronic control unit 100. The weight values are digitalized by a digital voltmeter 102 (type 3478A, Hewlett-Packard). A 2-channel X-t compensation line recorder 104 (Siemens, Munich/Germany, type Compensograph X-TM73921) is used for data recording.

Means may be provided for optically displaying the weight, mass and temperature values and to process the values by an electronic data processing system. The data processing system may also be used for controlling the sequence of operations necessary for a density measuring experiment.

The measuring vessel which encloses the sample support means and contains the buoyant or sample liquid has preferably more than one jacket, e.g. two, three or four jackets for receiving a heat exchange fluid for temperature control and for buffering and heat insulation purposes.

Figure 3:
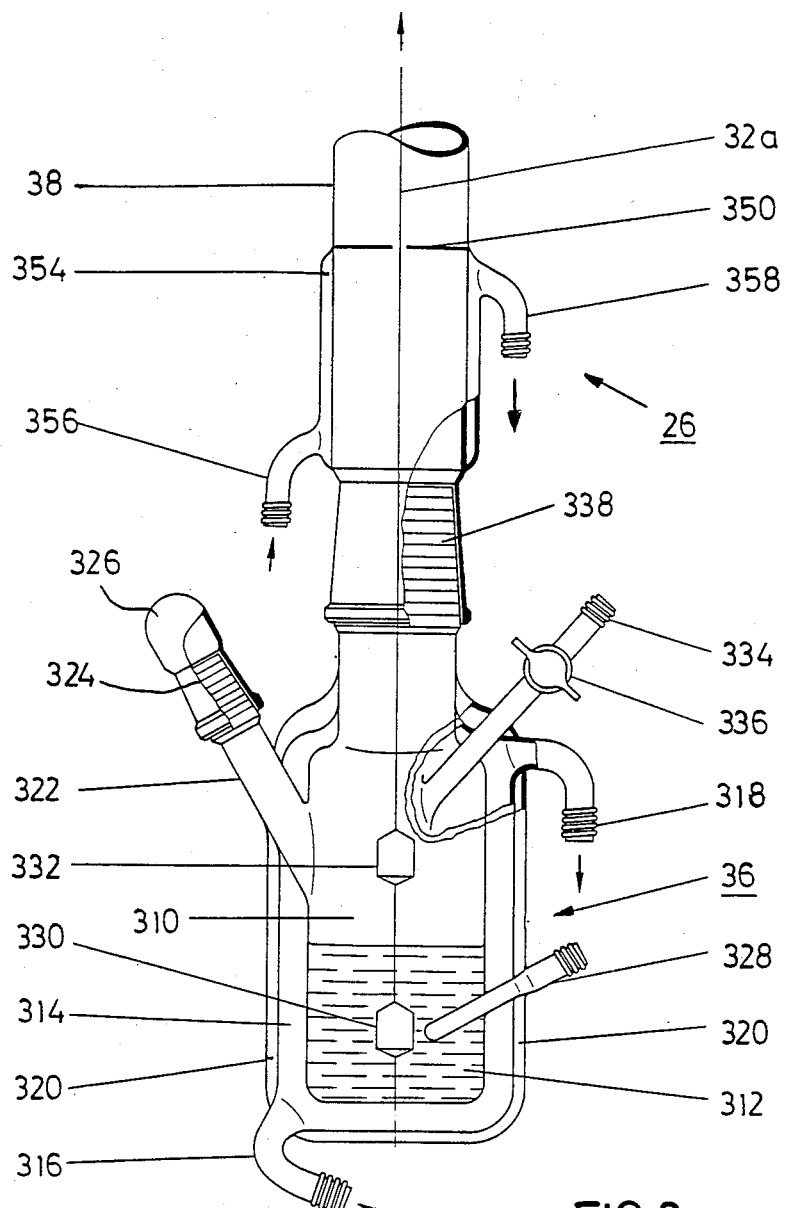
FIG. 3 is a more detailed sectional view of a measuring chamber portion of the apparatus of FIG. 1.

FIG. 3 shows a preferred embodiment of a measuring vessel 36 which has two jackets. The vessel 36 shown in FIG. 3 forms an inner chamber 310 for receiving a buoyant liquid 312. The chamber 310 is enclosed by an inner jacket 314 defined by a pair of essentially concentric cylindrical walls and having an entrance tube 316 and an exit tube 318 for circulating a temperature control fluid. The tubes 316, 318 are adapted to being coupled by flexible conduits to the unit 12 (FIG. 1). The inner chamber 310 may comprise a magnetic stirring device (not shown). The inner jacket 314 is heat-insulated against the surrounding environment by an evacuated outer jacket 320 which is similar to a Dewar bottle.

According to an aspect of the present invention, an upper part of the chamber 310 communicates with a tube section 322 with extends upwards and outwards through the jackets 314, 320 and has an outer end which may be provided with a ground conical end 324 adapted to be closed by a mating ground cap 326. Alternatively, the tube 322 may be provided with a cock. The tube 322 serves for manipulating and introducing samples and may also be used for introducing a cannula for modifying or exchanging the buoyant or sample liquid.

A tube 328 adapted to receive a temperature sensor or probe (not shown) and having a closed inner end extends from the outside through the jackets 314, 316 into a lower portion of the chamber 310. The tube 328 may be filled with a liquid for improving the thermal coupling between the buoyant fluid and the temperature sensor. In the case of low temperature experiments, the coupling fluid should have a sufficiently low freezing point and may comprise methanol, ethanol, tuluene, isopentene and other suitable liquids. In the case of high temperature experiments, the coupling liquid should have a sufficiently high boiling point and may comprise glycol, glycerol, silicone oil and the like. The temperature sensor may comprise a resistance thermometer or a thermocouple. The closed inner end of the tube 328 is positioned within the buoyant liquid 312 near a lower stirrup weighing pan 330 of the weighing hangdown assembly. The lower weighing pan 330 is immersed into the buoyant liquid 312 and is suspended by a length of thin wire from an upper stirrup weighing pan 332 which is positioned above the level of the buoyant liquid 312 and is in turn connected by the thin wire 32a to the balance beam 28 (FIG. 1). The pans 330, 332 serve as sample support means.

The vessel 36 is further provided with a gas outlet 334 which leads from the chamber 310 to the atmosphere and can be closed by a ground glass stopcock 336. The measuring vessel 36 is removably coupled to the lower end of the protective tube 38 by a ground joint 338.

Figure 4:
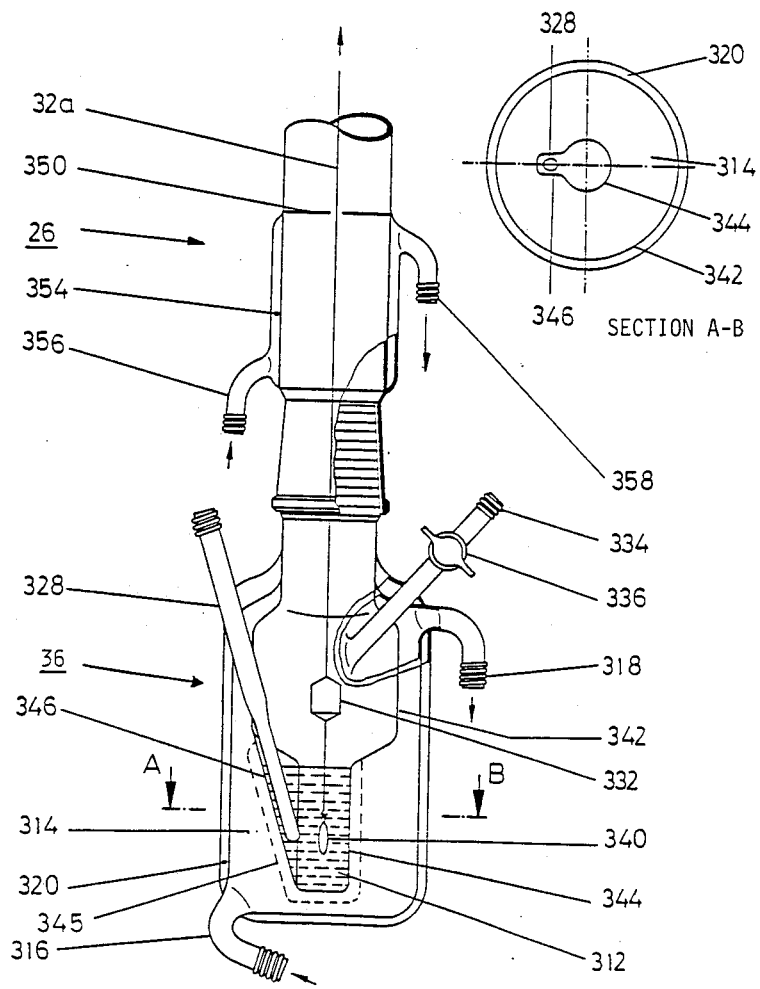
FIG. 4 shows a modification of the measuring chamber portion of FIG. 3.

The modified measuring vessel shown in FIG. 4 is similar to that of FIG. 3 and the same reference numerals have been used for similar parts. The embodiment of FIG. 4 is specifically suited for measuring the density of small liquid samples (usually up to 5 to 10 cm$^3$). The modified hangdown assembly shown in FIG. 4 comprises a small sinker 340 of fused silica (volume about 0.1 cm$^3$, weight about 0.2 grams) which replaces the lower stirrup pan 330 of FIG. 3. The sinker 340 may be suspended from the upper strirrup pan 332 or directly on the wire 32a. Further, the lower part of the wall 342 of the measuring chamber forms a small diameter tubular extension 344 which receives the liquid sample 312, the density of which is to be measured. The tubular extension 344 may have a volume of about 6 cm$^3$ or somewhat more. The extension 344 has a lateral bulge 346 which tapers downwardly and encloses a temperature sensor tube 328 which extends steeply upwardly for reducing the sample volume space. The inner jacket 314 has a relatively large radial thickness adjacent the tubular extension 344 and, thus, forms a relatively large thermal buffer volume. A further buffer volume jacket 345 may directly surround the extension 312, as shown by a broken line to provide an additional mechanic and thermic insulation of the sample volume. A four-jacket embodiment of the invention will be explained with reference to FIGS. 6 and 7.

FIG. 5 shows the lower portion of the protective tube 38 which is provided with a preferred embodiment of the separator and barrier means which acts just as a semipermeable, quasi-adiabatic wall separating the measuring chamber and the weighing chamber thermodynamically in order to enable free variation of the measuring temperature in the measuring chamber while maintaining constant the temperature and the pressure in the weighing chamber. This barrier means forms an essential aspect of the present invention. In the embodiment shown in FIG. 5, the barrier means 26 comprises a diaphragm 350 having a relatively narrow aperture 352 through which the wire 32a of the measuring hangdown assembly extends. The aperture 352 may have e.g. circular, oval, triangular, quadratic, pentagonal or other shapes. Preferred is the shape of an elongated slit or of two crossing slits. The diaphragm 350 separates the measuring chamber 24 formed by the measuring vessel 36 and the lower portion of the protective tube 38 from the weighing chamber 22 in which the balance beam and the weighing hangdown assembly are positioned. A cooling jacket 354 surrounds the portion of the protective tube 38 between the diaphragm 350 and the ground joint. The cooling jacket 354 has an inlet 356 and an outlet 358 for circulating a cooling fluid and serves to condense the vapors of the buoyant or sample liquid produced in the measuring vessel and in combination with the diaphragm 350 prevents these vapors from entering the weighing chamber 22. A condensate collector 360 is mounted in the lower portion of the protective tube and provided with a condensate draining conduit 362 in form of a thin glass tube which has a coil portion 364 and ends in the measuring vessel 36 (not shown in FIG. 5) below the level of the buoyant or sample liquid so that the returning of the condensed liquid is effected with as little disturbances as possible.

The relatively long protective tube 38 forms a thermal transition region between the thermally insulated measuring chamber in the vessel 36 and the weighing chamber 22 so that the separator 26 and diaphragm 350, which practically act as an unidirectional conductive flow valve essentially attains the temperature of the weighing chamber even if some temperature gradient along the protective tube 38 may be produced by the condensator or cooling jacket 354.

In operation, preferably some pressure drop in the direction from the weighing volume 22 to the measuring volume 24 is maintained. A preferred value of this pressure drop is between 0 to about 10 kPa, most preferred between 0.2 to 2 kPa.

The exemplary separator and barrier device 26 described above acts just as a semipermeable, quasi-adiabatic wall separating the weighing chamber and the sample chamber thermodynamically. Thus, predetermined constant temperature and pressure conditions can be maintained in the portions of the envelope which comprise the balance beam, the force measuring system and the weighing hangdown assembly and, thus, constant buoyancy conditions for the weighing hangdown assembly and the compensating weights, independent of the conditions within the sample chamber.

Other embodiments of the barrier device 26 are possible, e.g. a diaphragm 350 made of a gas permeable sintered material may be used which has a hole for freely passing the wire 32a of the measuring hangdown assembly.

Figure 7:
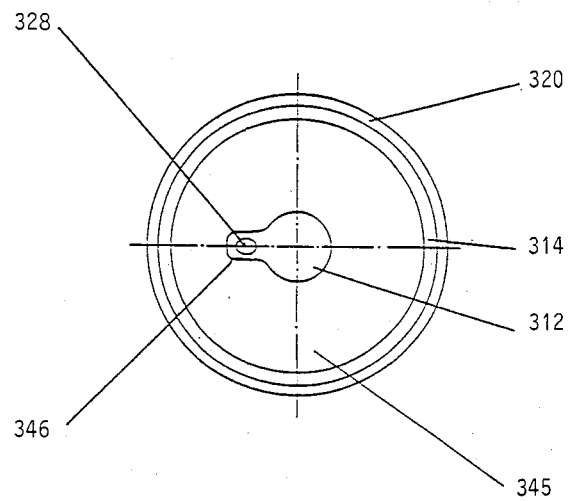
FIG. 7 is a cross-section along a line A-B in FIG. 6.
Figure 6:
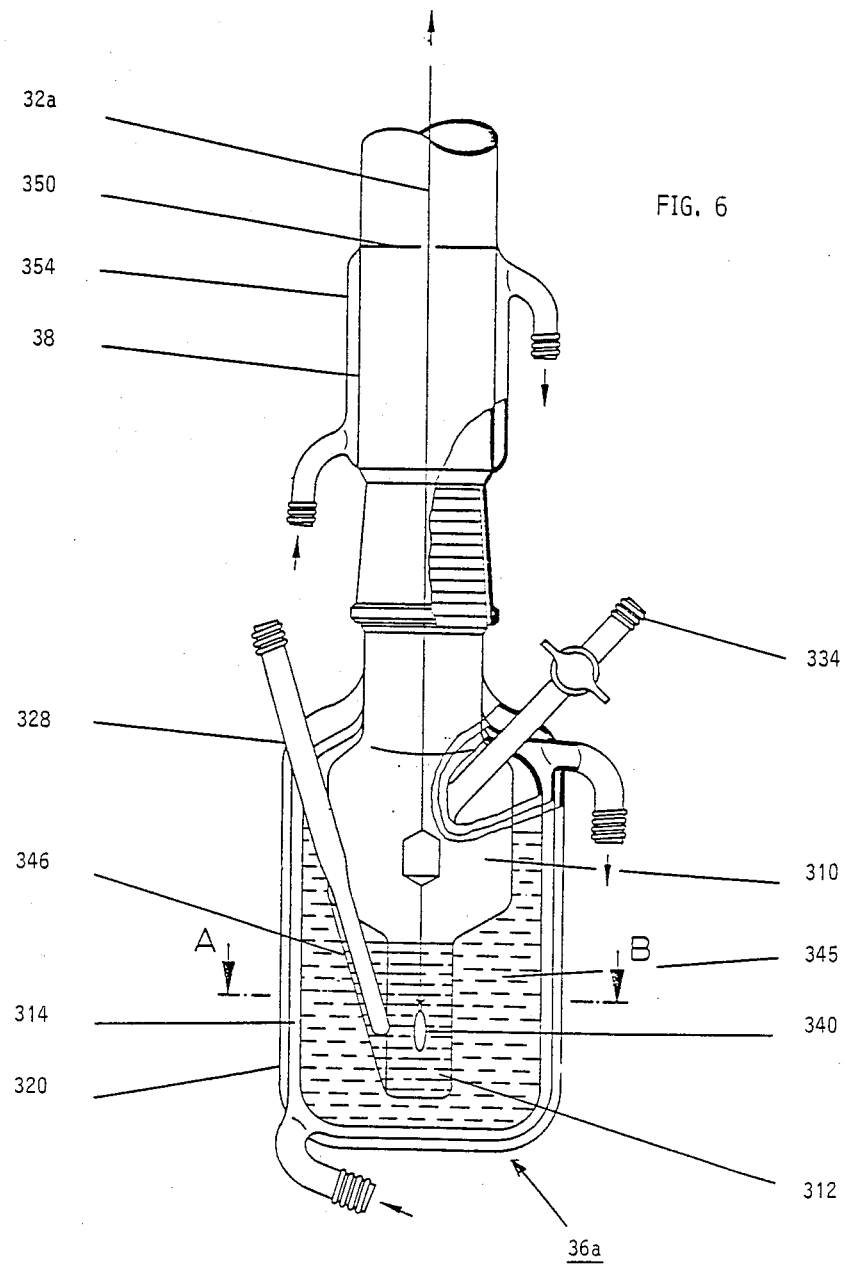
FIG. 6 shows a further embodiment of a multi-jacket measuring chamber for the apparatus of FIG. 1

FIGS. 6 and 7 show a four-jacket embodiment of a measuring vessel 36a which is similar to FIG. 4. The measuring chamber 310 is surrounded by a large volume buffer chamber 345 provided at their upper end, in the case of solids, with a filling tube which may be similar as the tube 322 of FIG. 3. The buffer volume 345 is filled with a liquid of an appropriate freezing or boiling temperature. The buffer volume 345 insulates the measuring chamber 312 against thermal and/or mechanical disturbations and stabilizes the measuring conditions.

The envelope, the various vessels and tubes and the components of the separator or barrier device may be made of glass as commonly used for chemical apparatuses. Of course, also other materials as quartz and/or porcellaine and/or ceramic and/or metal, as copper, brass, aluminum, stainless steel, titanium, and plasic materials as PTFE, PVC, polyamide, polyformaldehyde, polyester, curable resins, polyurethane, polyaramide, polyvinylcarbazol and so on may be used. Depending on the material, also joints other than ground joints may be used, flange joints.

In operation, when the density of a solid substance is to be measured with the apparatus as described above a sample of the substance in question is first placed on the weighing pan 322 (FIG. 3) which is above the buoyant liquid 312, and the weight of the sample is measured. Then, the sample is put on the weighing pan 330 immersed in the buoyant liquid 312 and the weight is again measured. The density is derived from the difference of the weight values obtained, as well known in the art.

Bodies having a simple, e.g. cylindrical configuration and preferably made of transparent, annealed top quality fused silica (Homosil (TM), Heraeuc Quarzschmelze, Hanau/Germany, may be used as calibration standard for calibrating the densitometer. The surface of the cylindrical calibration bodies is optically ground and polished with outmost precision and the dimensions, i.e. the volume of the body is determined by laser-interferometric measurements.

It has been already mentioned that it is preferred to maintain a pressure difference across the separator or barrier device 26 during the measurements, more specifically, the weighing chamber should be maintained at a higher pressure than the measuring chamber. This can be easily effected with the apparatus of FIG. 1 by setting the immersion tube arrangement 50 at a higher pressure than the immersion tube arrangement 110 so that the protective gas flows through the diaphragm 350 to produce the desired pressure drop.

Various changes and modifications can be made to the above described preferred embodiment without departing from the scope of the claims. The immersion tube arrangement may comprise liquids other than glycerol or mercury, e.g. silicon oil. The heating of the measuring vessel may also be effected by other heating means, e.g. by inductive high-frequency heating, electrical resistance heating, radiation heating or a combination of such heating means, and cooling may be effected e.g. by Peltier elements. The regulation of the protective gas pressure and of the pressure drop across the barrier may be effected by means other than the described immersion tube arrangement, e.g. by manostats, manostat circuits, pressure reducing valves and similar devices. In the course of the measuring of the temperature-dependency of the density of a sample, the buoyant liquid may be varied continuously or discontinuously in respect to its chemical type, amount and composition or even completely exchanged which may be effected by applying pressure or suction by means of suction and/or pressure pumps and/or suitable connections to the measuring vessel. The measuring vessel may be provided with a plurality of temperature probes and/or a plurality of manipulating tubes and/or a plurality of closable connections to the outer atmosphere. The asymmetrical blocking device may comprise a plurality of diaphragms and/or cooling devices or jackets and/or condensate return devices, baffles and the like which may be positioned in spaced relationship along the flow path from the measuring chamber to the sample chamber.

I claim:

1. An apparatus for measuring the density of a sample of condensed matter on the basis of hydrostatic method, said apparatus comprising:
   a vacuum and monostatic inert gas system for delivering an inert gas of predetermined pressure;
   an airtight envelope forming a weighing chamber and a measuring chamber, said weighing chamber having a port connected to said gas system for receiving said inert gas of predetermined pressure;
   a balance including a force sensitive system and a measuring hangdown assembly connected to said force sensitive system, said force sensitive system being positioned within said weighing chamber and said measuring hangdown assembly extending from said weighing chamber into said measuring chamber, said measuring chamber having a bottom portion for receiving a buoyant liquid;
   barrier means for thermodynamically separating said weighing chamber and said measuring chamber, said barrier means essentially preventing condensable vapors from flowing from said measuring chamber into said weighing chamber while allowing an exchange of inert gas between said chambers; said measuring hangdown assembly extending through said barrier means, said barrier means forming a gas flow path from said measuring chamber through said weighing chamber to said inert gas system, said flow path being the only inert gas flow path existing during a density measurement; and
   cooling means for condensing vapors produced in said measuring chamber, said cooling means being positioned on the side of the barrier means which faces the measuring chamber.

2. The apparatus as claimed in claim 1, wherein said measuring hangdown assembly comprises an elongated delicate suspension member and said barrier means comprises at least one diaphragm which has an aperture through which said suspension member extends.

3. The apparatus as claimed in claim 2, wherein said aperture has the shape of an elongated slit.

4. The apparatus as claimed in claim 2, wherein said aperture has the shape of a pair of crossed slits.

5. The apparatus as claimed in claim 1, wherein said condensing means comprises condensate collecting means.

6. The apparatus as claimed in claim 5, wherein said condensate collecting means is provided with means for returning the condensate to the liquid which has produced said vapors.

7. The apparatus as claimed in claim 5 including a condensate returning conduit extending from said collecting means to a location in said bottom portion of said measuring chamber.

8. The apparatus as claimed in claim 1 wherein said measuring chamber comprises a measuring vessel which has access means permitting to access an inner volume of said vessel from the outside; said access means being provided with closure means.

9. The apparatus as claimed in claim 1, wherein said measuring chamber comprises a measuring vessel adapted to receive said liquid and being provided with a temperature probe tube projecting into the inner volume of said vessel.

10. The apparatus as claimed in claim 1, wherein said measuring chamber comprises a measuring vessel which has a lower portion of reduced cross section.

11. The apparatus as claimed in claim 1, wherein said measuring chamber comprises a multi-jacket measuring vessel.

12. The apparatus as claimed in claim 11, wherein said measuring vessel comprises a first jacket for circulating a temperature control fluid and at least one further, second, insulating jacket surrounding said first jacket.

13. The apparatus as claimed in claim 11 wherein said multi-jacket measuring vessel is a unitary, integral structure.

14. The apparatus as claimed in claim 1, wherein said measuring chamber comprises a measuring vessel having a portion of receiving said buoyant liquid, and a buffer chamber surrounding said portion and adapted to receive a buffer liquid.

15. The apparatus as claimed in claim 1, wherein at least one of said weighing and measuring chambers are connected to a vacuum and gas system which comprises means for pressure control.

16. The apparatus as claimed in claim 1, further comprising a tube connected to said measuring chamber to allow access to said bottom portion for varying said buoyant liquid.

17. The apparatus as claimed in claim 1 characterized by means for producing a pressure drop across said barrier means.

18. The apparatus as claimed in claim 1 wherein said measuring chamber is surrounded by at least two jackets, said measuring chamber and said jackets forming an integral device.

19. A densitometer for measuring the density of solids and liquids at a predetermined temperature comprising:
   a measuring arrangement operating on the hydrostatic buoyancy principle and including an electrobalance, said measuring arrangement comprising a two-chamber measuring system having a measuring chamber and a weighing or balance chamber:
   a semipermeable quasi-adiabatic wall means for semipermeably and quasiadiabatically separating the chambers, the wall means forming an asymmetrical thermodynamic barrier between the chambers, and
   means for selecting the thermodynamic conditions of state within said measuring chamber relative to temperature or pressure while the thermodynamic conditions of state within said weighing chamber are separately fixed.

20. The densitometer as claimed in claim 19, wherein the absoluteness of the density measurements is effected by means of a calibration standard made of fused silica.

* * * * *